(12) United States Patent
Desoutter et al.

(10) Patent No.: US 10,239,135 B2
(45) Date of Patent: Mar. 26, 2019

(54) SURGICAL SAW MOUNT AND BLADE

(71) Applicant: De Soutter Medical Ltd, Aylesbury (GB)

(72) Inventors: George Desoutter, Aylesbury (GB); Chris Block, Aylesbury (GB)

(73) Assignee: De Soutter Medical Ltd, Aylesbury (GB)

( * ) Notice: Subject to any disclaimer, the term of this patent is extended or adjusted under 35 U.S.C. 154(b) by 0 days.

(21) Appl. No.: 15/945,829

(22) Filed: Apr. 5, 2018

(65) Prior Publication Data
US 2018/0221973 A1    Aug. 9, 2018

Related U.S. Application Data

(63) Continuation of application No. 14/767,402, filed as application No. PCT/GB2014/050646 on Mar. 5, 2014.

(30) Foreign Application Priority Data

Mar. 6, 2013 (GB) .................................. 1304019.1

(51) Int. Cl.
*A61B 17/00* (2006.01)
*B23D 51/10* (2006.01)
*A61B 17/14* (2006.01)

(52) U.S. Cl.
CPC ............ *B23D 51/10* (2013.01); *A61B 17/142* (2016.11)

(58) Field of Classification Search
CPC combination set(s) only.
See application file for complete search history.

(56) References Cited

U.S. PATENT DOCUMENTS

| | | | |
|---|---|---|---|
| 4,386,609 A | 6/1983 | Mongeon |
| 5,382,249 A | 1/1995 | Fletcher |
| 5,439,472 A | 8/1995 | Evans et al. |
| 5,553,675 A | 9/1996 | Pitzen et al. |
| 5,694,693 A | 12/1997 | Hutchins et al. |
| 5,839,196 A | 11/1998 | Trott |
| 6,113,618 A | 9/2000 | Nic |

(Continued)

FOREIGN PATENT DOCUMENTS

| | | |
|---|---|---|
| DE | 102008062880 A1 | 6/2010 |
| DE | 102008063239 A1 | 6/2010 |

(Continued)

*Primary Examiner* — Sameh Boles
(74) *Attorney, Agent, or Firm* — Winstead PC

(57) ABSTRACT

There is disclosed a sagittal saw blade mount and corresponding sagittal saw blade. The blade mount is configured to rotationally oscillate along a plane of motion about an axis of rotation which passes through the blade mount crossing the plane of motion at a point of rotation. The blade mount comprises a securing portion comprising two securing faces passing through the plane of motion and a locking member configured to urge a blade towards the securing portion in a first direction parallel to the plane of motion, thereby securing the blade between the locking member and the securing faces. The two securing faces are angled such that the planes of the securing faces intersect with each other and with the plane of motion at a point of intersection which is positioned such that the point of rotation lies between the point of intersection and the securing portion.

6 Claims, 9 Drawing Sheets

(56) References Cited

U.S. PATENT DOCUMENTS

| | | |
|---|---|---|
| 6,113,619 A | 9/2000 | Pascaloff |
| 6,503,253 B1 | 1/2003 | Fletcher et al. |
| 2004/0243136 A1 | 12/2004 | Gupta et al. |
| 2006/0009796 A1 | 1/2006 | Carusillo et al. |
| 2006/0217729 A1* | 9/2006 | Eskridge .............. A61B 17/162 606/80 |
| 2006/0272468 A1 | 12/2006 | Gupta et al. |
| 2007/0016238 A1 | 1/2007 | Marietta |
| 2007/0119055 A1 | 5/2007 | Walen et al. |
| 2007/0123893 A1 | 5/2007 | O'Donoghue |
| 2008/0027499 A1 | 1/2008 | Srivathsa et al. |
| 2009/0312761 A1 | 12/2009 | Boykin et al. |

FOREIGN PATENT DOCUMENTS

| | | |
|---|---|---|
| JP | 2008-029848 A | 2/2008 |
| JP | 2009-501059 A | 1/2009 |
| WO | WO-2005104964 A1 | 11/2005 |
| WO | WO-2012021771 A2 | 2/2012 |

\* cited by examiner

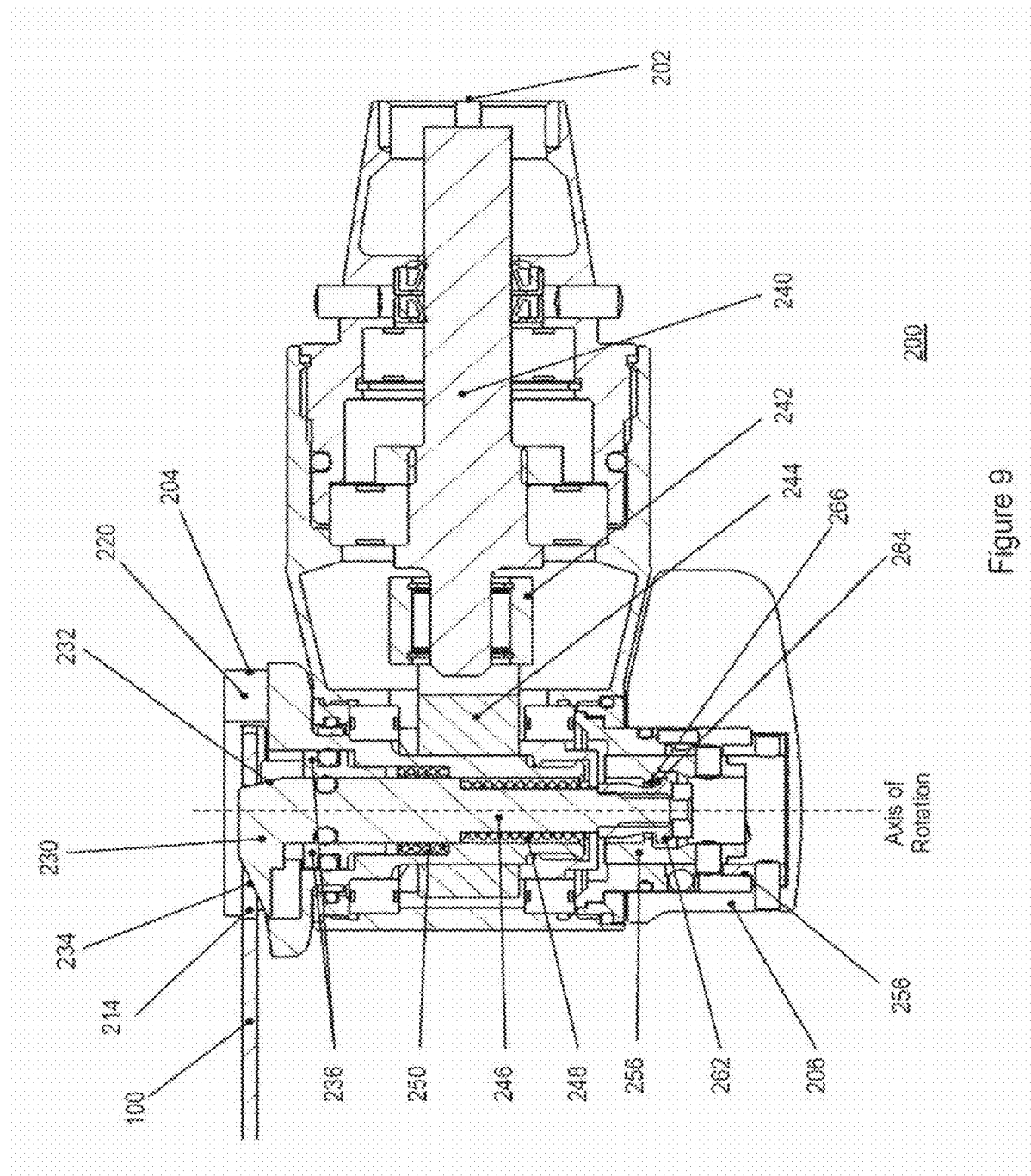

such a sagittal saw. A typical powered saw has a handpiece and a
SURGICAL SAW MOUNT AND BLADE This patent application is a continuation of U.S. patent application Ser. No. 14/767,402. U.S. patent application Ser. No. 14/767,402 is a national-stage filing of International Patent Application No. PCT/GB2014/050646, which was filed on Mar. 5, 2014. Each of U.S. patent application Ser. No. 14/767,402 and International Patent Application No. PCT/GB2014/050646 is incorporated by reference.

FIELD OF THE INVENTION

Embodiments of the present invention generally relate to surgical saws and blades. More particularly, embodiments relate to a blade mount for removably coupling a saw blade to an oscillatory power tool. Further embodiments of the invention relate to a saw blade with a coupling portion for securely mounting the blade in a corresponding blade mount.

BACKGROUND

Orthopaedic surgeons are regularly required to cut bone and other hard tissue during surgical procedures. To achieve this, surgeons usually make use of powered tools, such as sagittal saws. A typical powered saw has a handpiece and a blade mount in which a surgical blade may be secured. The handpiece usually houses either an electrically or pneumatically driven motor. The motor drives the blade mount which, in turn drives the saw blade. The saw blades are usually removably coupled to the blade mount such that they may be replaced. This is particularly important for surgical saws due to the need to sterilise any tools which are used during a surgical procedure. However, due to the need to accommodate additional space within the mount to allow the blade to be easily slid in and out, as well as the necessary manufacturing tolerances resulting from fabrication of the parts, the blades cannot be fit perfectly to the blade mount. This may result in movement between the mount and the blade causing the mount to wear down through repeated use.

Two varieties of powered saws are sagittal saws and reciprocating saws. Sagittal saws drive the blade mount to rotate side to side. This oscillatory rotation results in sagittal saw blades pivoting about one end of the blade which is secured within the blade mount. A cutting edge, such as a serrated edge, is located at the distal end of the blade, running across the width of the blade. Reciprocating saws are driven to oscillate in line with the length of the blade. A cutting edge is located on one or more of the side edges running down the length of the blade.

Typically surgical saws use flat saw blades which are secured at a coupling portion at one end. The coupling portion of a sagittal saw blade usually comprises slots or openings into which coupling members, such as pins, may be received in order to secure the blade to a blade mount. In addition to these pins, the blade may be clamped against the base of the blade mount to secure it in place. Quick release mechanisms are available which allow for blades to be easily disengaged from blade mounts without the need for tools.

Due to the nature of the oscillatory action of a sagittal saw there is a large amount of force applied at the points of contact between the blade and the mount, particularly when the blade is changing direction. Due to the excess space within the blade mount, the blade may rub or strike surfaces of the blade mount, causing both the blade and the mount to wear. As the surfaces wear down, the blade may work loose therefore becoming less efficient and resulting in a less stable support for the blade. The excess movement of the blade within the mount may cause vibrations resulting in the blade cutting less accurately and causing noise which may be distracting to the surgeon. The reduced accuracy and stability of the saw and blade may increase operation times. There is therefore a need for a blade mount and corresponding blade which reduce mechanical play during operation and which accommodate for wear through repeated use.

SUMMARY OF INVENTION

According to one aspect of the invention there is provided a blade mount configured to rotationally oscillate in a plane of motion, about an axis of rotation which passes through the blade mount crossing the plane of motion at a point of rotation. The blade mount comprises a securing portion comprising two securing faces and a locking member configured to urge a blade towards the securing portion in a first direction parallel to the plane of motion thereby securing the blade between the locking member and the securing faces. The two securing faces are angled such that the planes of the securing faces intersect with each other and with the plane of motion at a point of intersection such that the point of rotation lies between the point of intersection and the securing portion.

By securing a blade by urging the blade along the plane of motion, the blade mount may more effectively secure and drive the blade. This is enhanced by the securing faces being angled relative to each other, resulting in the force exerted by the locking member being transferred into transverse forces directed along the plane of motion. The majority of the stress upon the blade as it is driven is likely to be in the plane of motion. The locking member can account for any excess movement of the blade within the blade mount by urging the blade back against the securing faces. Furthermore, any wear at the surfaces of the blade mount and/or the blade may lead to a less tight fit and therefore result in the unwanted blade movement within the blade mount. This may cause the blade to be driven less securely, to wear quicker and may also cause excess noise due to the blade rattling within the mount. By urging the blade against the securing faces, the locking member may adjust to any wear or excess blade movement in order to maintain a secure fit.

The securing members are angled relative to each other, forming a wedge arrangement upon which a blade may be urged by the locking member. When a blade is secured within the blade mount, the securing members help to drive the blade. A large proportion of the forces which drive the blade to rotate are applied at the securing faces. Each securing member defines a plane. The two planes of the securing member intersect in the plane of motion at a point of intersection. By angling the securing members such that this point of intersection is located on the far side of the axis of rotation to the securing members, each securing face may apply a driving force which has a component which urges the blade further into the blade mount. This provides a more secure drive for the blade and reduces relative movement and wear between the mount and the blade. It is beneficial for the securing faces to be perpendicular to the plane of motion so that the driving forces are parallel to the plane of motion.

If the angle between the two planes defined by the securing faces is too small, a blade could potentially get jammed within the blade mount. Conversely, if the angle is too great, the securing faces would be unable to provide large enough transverse forces to drive and/or secure the blade effectively. It is advantageous for the angle in the plane of motion between the two planes of the securing faces at the point of intersection to be greater than 20°. Furthermore, it is advantageous for this angle to be less than 40°. It is beneficial for this angle to be greater than 25°. In addition, it is beneficial for this angle to be less than 35°. It is preferable for this angle to be greater than 28°. It is also preferable for this angle to be less than 32°. The inventors have found that an angle of 30° between the two planes of the securing faces is a good compromise between driving the blade to rotate whilst maintaining a secure fit without risking the blade jamming within the blade mount.

In order to help secure the blade effectively, the blade mount may further comprise a base upon which a blade may lie. The base may have a base face which runs parallel to the plane of motion. The locking member and securing members may protrude out of the base. In addition, the blade mount may further comprise an upper face running parallel to the base face. The upper face may face the base face and may be displaced from the base face to allow a blade to be slid between the base face and the upper face. The upper face and the base face help to secure the blade and help to prevent blade movement out of the plane of motion.

In addition to urging the blade towards the securing faces, the locking member may also urge the blade against the upper face of the blade mount. This helps to secure the blade and prevent movement out of the plane of motion. The locking member may be configured to be urged out of the base of the blade mount, in a second direction. The second direction may be perpendicular to the plane of motion. The locking member may urge the blade towards the securing faces, along the first direction, and towards the upper face, along the second direction, by urging the blade at a first inclined face of the locking member. The inclined face of the locking member may be inclined relative to the first and second directions. In addition to urging the blade against the securing faces and the upper face, the inclined face may account for wear in either the locking member or the blade. If either the blade or the blade mount has been worn down, the locking member may be urged further out of the base of the blade mount until the inclined face makes contact with and secures the blade within the blade mount.

In order to allow a blade to be inserted into the blade mount, it may be beneficial for the locking member to be able to retract into the base of the blade mount, out of the path of the blade. The locking member may be configured to be retracted into the base such that it no longer protrudes out of the base face. Once the blade has been inserted at least partially past the locking member, the locking member may be urged against a face or edge of the blade in order to secure the blade as described above. The locking member may comprise a second inclined face, inclined relative to the first and second directions. A blade which is inserted into the blade mount may make contact with the second inclined face and urge the blade into the base of the blade mount.

The blade mount may be made from metal, such as surgical steel, or any other strong, durable material. The blade mount is suitable for securing a sagittal saw blade. The blade mount may form part of an oscillatory power tool or may form part of an attachment suitable for being attached to a power tool. The rotational oscillation of the blade mount may be driven by a motor which may be located within an oscillatory power tool. Where the blade mount forms part of an attachment, the attachment may comprise a mechanism to convert a rotary drive provided by a power tool into a rotational oscillation provided to the blade mount. The attachment or power tool comprising the blade mount may include a mechanism for releasing a blade from the blade mount. The release mechanism may be isolated from the blade mount such that it doesn't rotate with the blade mount. This reduces the mass which must be driven and therefore provides a more efficient and stable drive.

In accordance with a second aspect of the invention, there is provided a surgical saw blade comprising a substantially planar body comprising a distal and a proximal end defining a longitudinal axis lying in the plane of the blade. The distal end has a cutting edge and the proximal end forms part of a coupling portion for removably coupling the blade to an oscillatory power tool. The coupling portion is configured to be driven such that the blade rotationally oscillates about an axis of rotation running perpendicular to the plane of the blade and crossing the plane of the blade at a point of rotation. The coupling portion comprises a lock face perpendicular to the longitudinal axis of the blade and passing through the plane of the blade, the lock face forming part of a boundary of an aperture, the aperture extending through the plane of the blade. The coupling portion further comprises two prongs protruding from the proximal end of the blade. Each prong comprises an inner face. The inner faces are angled relative to the longitudinal axis of the blade such that the planes of the inner faces intersect with each other and with the plane of blade at a point of intersection located between the axis of rotation and the distal end of the blade.

The inner faces of the prongs of the blade allow the blade to be driven more securely than traditional surgical blades. Traditional surgical blades are driven from parallel edges of the blades, or by pins which are inserted through holes in the blades. By providing prongs on the blade with angled inner faces, the blade may be driven such that it is urged back into a blade mount, against the members of the mount doing the driving. The prongs may form wedge shapes which may be wedged into a blade mount to help secure the blade. The inner face of each prong is the face of the prong closest to the opposing prong. The inner faces of the prongs are angled such that the planes defined by the faces intersect at a point located between the distal end of the blade and the point of rotation. This means that a component of a driving force applied at one of the inner faces is directed such that it urges the blade further into a blade mount, resulting in a more secure driving action.

The blade may be secured in the plane of the blade due to the combination of the lock face and the two inner faces. The lock face, running perpendicular to the longitudinal axis of the blade, allows the blade to be urged along the longitudinal axis, urging the inner faces against one or more securing faces of a blade mount. As the inner faces of the prongs are angled relative to the longitudinal axis, this means that a longitudinal force provided at the lock face may be converted into transverse forces at the inner faces. Advantageously, the prongs may be symmetrical about the longitudinal axis resulting in equal and opposite the transverse forces when the blade is stationary. By allowing the blade to be secured by forces in the plane of the blade, relative movement between the blade and a blade mount is reduced, allowing the blade to be driven more stably and decreasing wear. Furthermore, wear between the blade and a blade mount may be accounted for by the angled inner faces of the blade. The inner faces of the prongs may be perpendicular to the plane of the blade in order to ensure that driving forces applied at the inner faces are directed along the plane of the blade.

If the angle between the two planes defined by the inner faces is too small, the driving forces could result in the blade becoming jammed within a blade mount. Conversely, if the angle is too great, the inner faces would be unsuitable for receiving a transverse force capable of driving and/or securing the blade effectively. It is advantageous for the angle in the plane of the blade between the two planes of the inner faces at the point of intersection to be greater than 20°. Furthermore, it is advantageous for this angle to be less than 40°. It is beneficial for this angle to be greater than 25°. In addition, it is beneficial for this angle to be less than 35°. It is preferable for this angle to be greater than 28°. It is also preferable for this angle to be less than 32°. The inventors have found that an angle of 30° between the two planes of the inner faces is a good compromise between the inner faces being capable of receiving rotational driving forces whilst maintaining a secure fit without the risking the blade jamming within a blade mount.

The blade is suitable for use with the above mentioned blade mount. The blade may be a sagittal saw blade. The blade may be made from metal, such as surgical steel, or any other sufficiently hard and durable material.

BRIEF DESCRIPTION OF THE DRAWINGS

In the following, embodiments of the present invention will be described by way of example only and with reference to the drawings in which.

DETAILED DESCRIPTION

Figure 1:
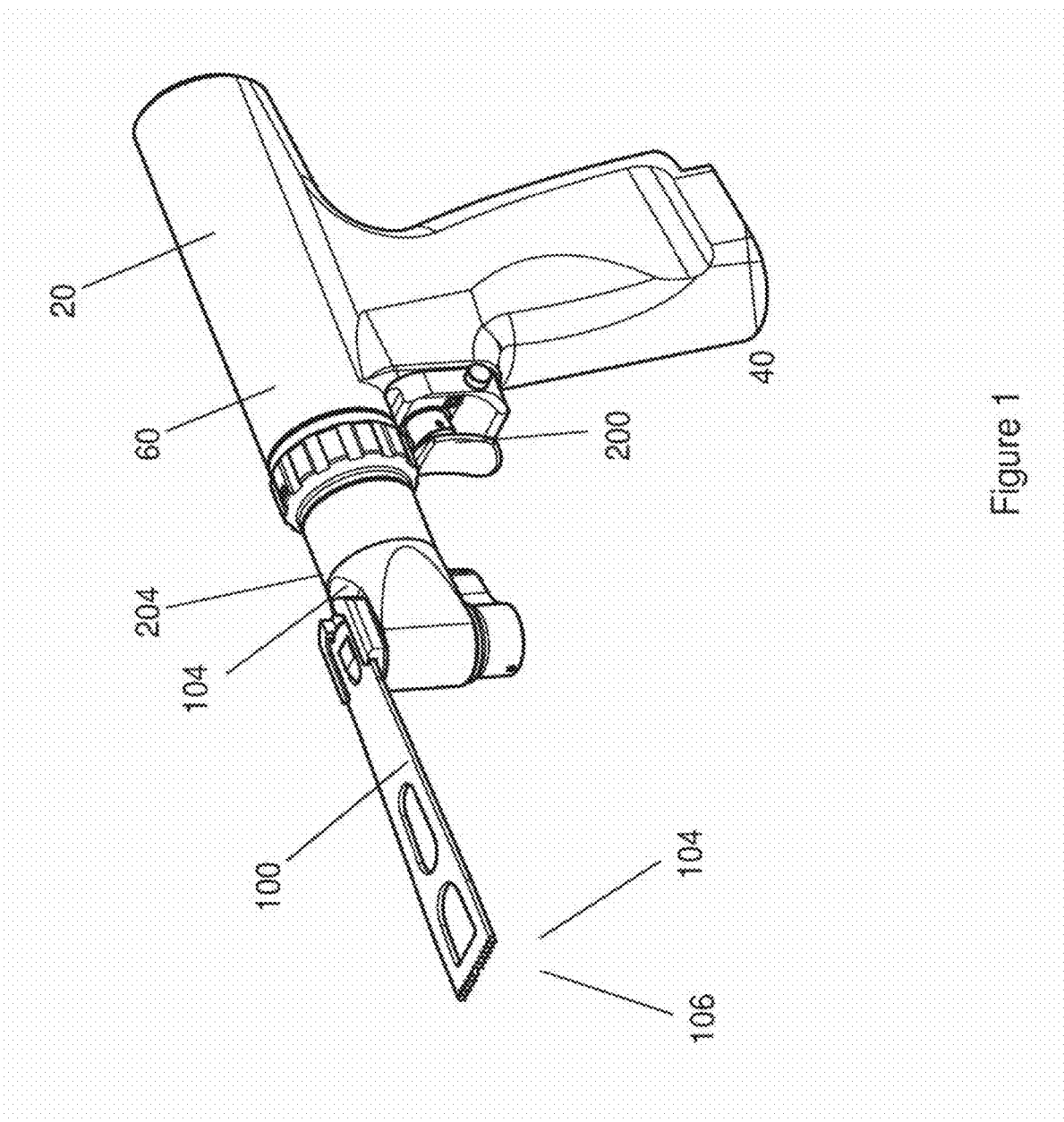
FIG. 1 shows a sagittal saw in accordance with an embodiment of the invention.

FIG. 1 shows a sagittal saw in accordance with an embodiment of the invention. The saw comprises a saw blade 100, a handpiece 20 and an attachment 200. The handpiece 20 comprises a handle 40 and a socket 60 for receiving the attachment 200. The attachment 200 comprises a blade mount 204 for securing the saw blade 100 to the attachment 200. The saw blade 100 has a cutting edge 106 located at the distal end 104 of the blade 100. The distal end 104 is the opposite end of the blade 100 from the proximal end 102 which is secured in the blade mount 204.

The handpiece 20 houses a motor which provides a rotary drive to the attachment 200. The attachment 200 uses the rotary drive to drive the blade mount 204 to rotationally oscillate. When a blade 100 is secured in the blade mount 204, the blade mount 204 drives the blade 100. This causes the blade 100 to rotationally oscillate in a plane of motion. It should be noted that, whilst a removable attachment 200 has been described, the features of the attachment 200 and the handpiece 20 may be integrated into a single tool.

Figure 2:
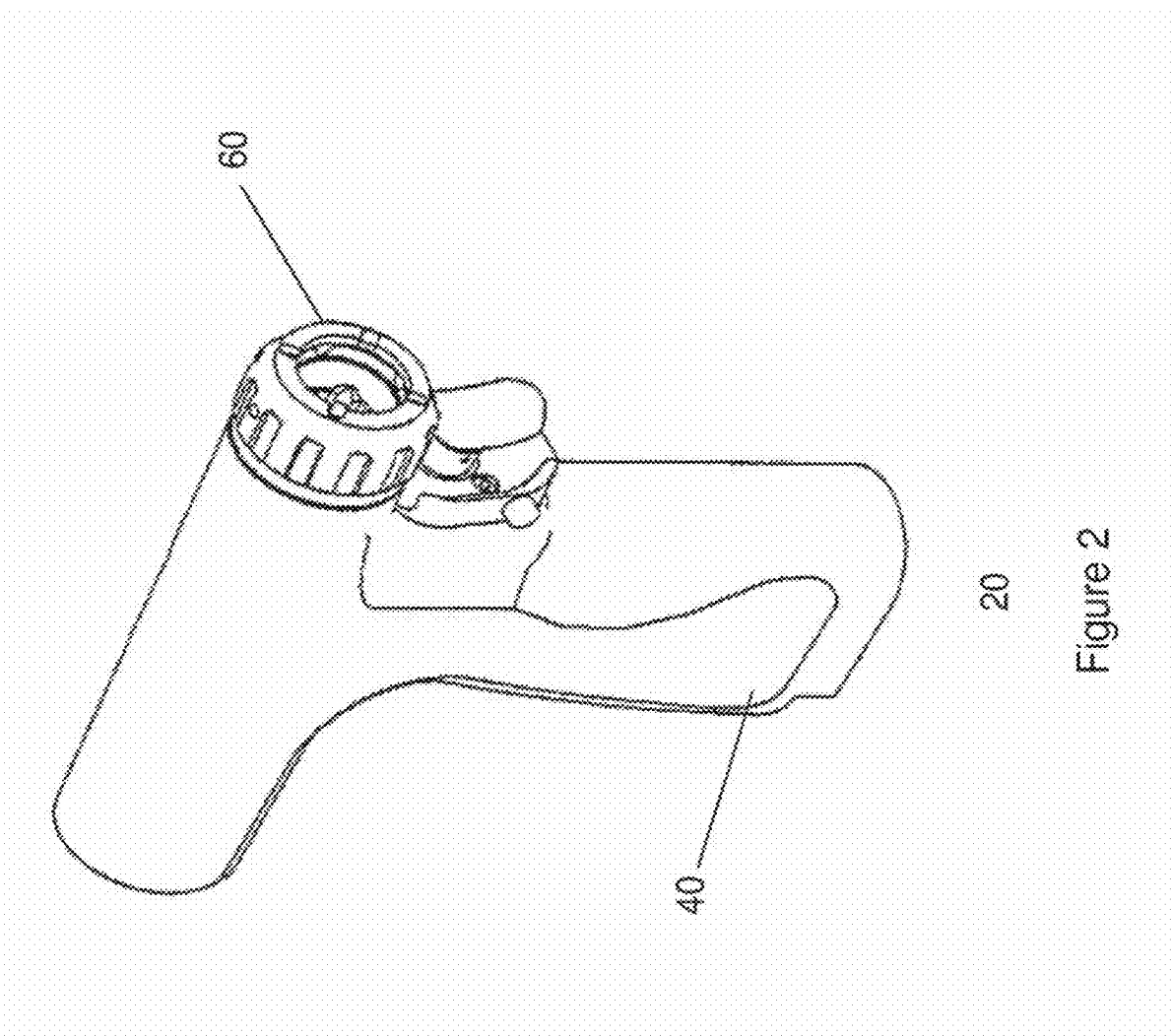
FIG. 2 shows a battery powered hand-piece 20 for a power tool.

FIG. 2 shows a battery powered hand-piece 20 for a power tool. The hand-piece 20 comprises a handle 40 and a socket 60 for connecting various attachments. A battery and motor are located within the hand-piece 20. The battery powers the motor which provides a rotary drive to any attachments secured in the socket 60. Whilst the specific embodiment depicted is battery powered, further embodiments of the invention may be pneumatically powered or may be powered by an external power source.

Figure 3:
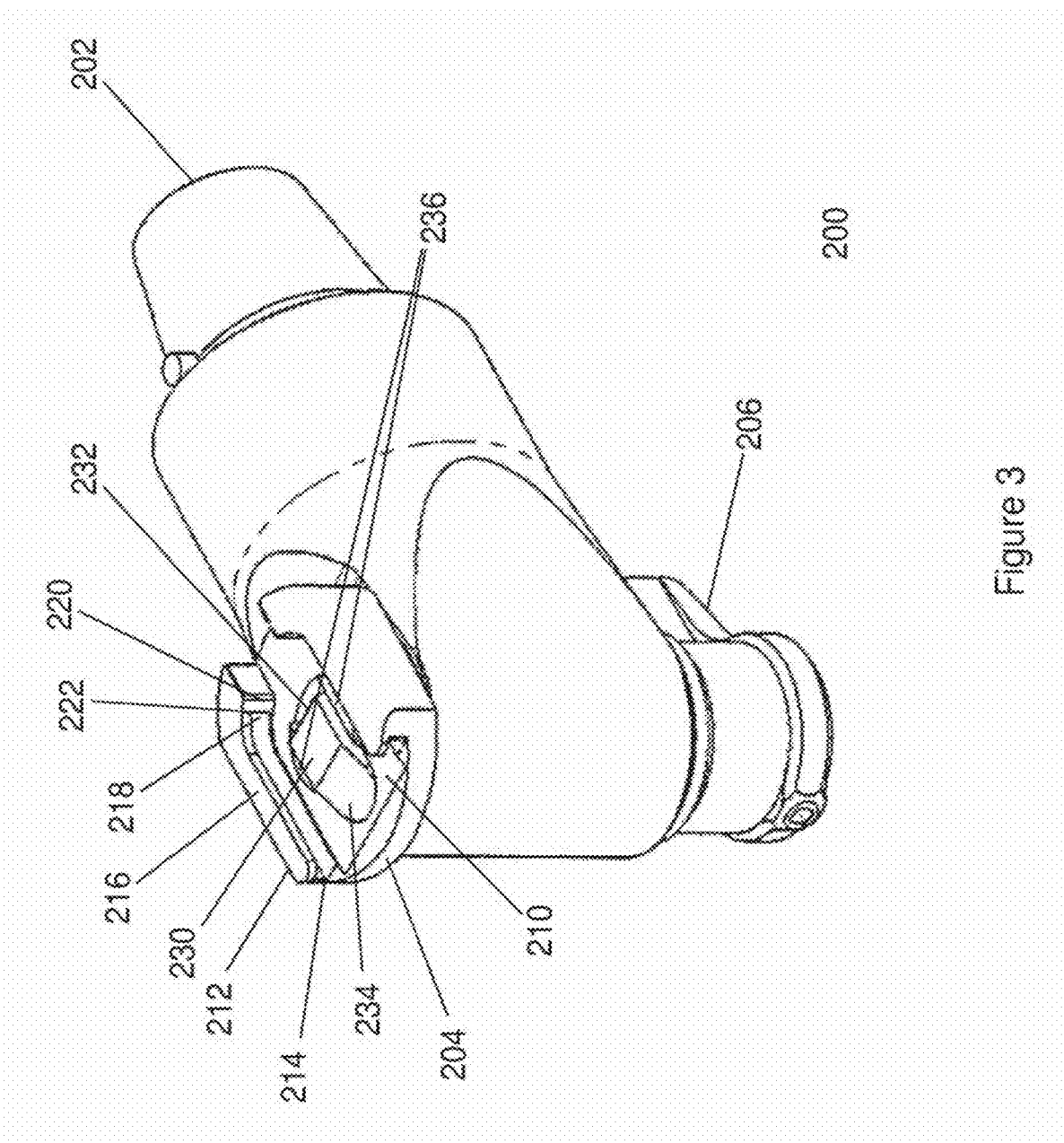
FIG. 3 shows a sagittal saw attachment 200 for a power tool in accordance with an embodiment of the present invention.

FIG. 3 shows a sagittal saw attachment 200 for a power tool in accordance with an embodiment of the present invention. The attachment 200 comprises a connector 202 at the proximal end of the attachment 200 for connecting the attachment to a socket 60 of a handpiece 20, a blade mount 204 at the distal end of the attachment 200 for securing and driving a blade 100, and a release knob 206 for releasing a secured blade 100 from the mount 204. A longitudinal axis of the attachment 200 runs from the proximal end of the attachment 200 to the distal end of the attachment 200. The attachment 200 is configured to receive a rotary drive from a socket 60 of a hand-piece 20. This drive is converted into an oscillatory motion in the body of the attachment 200. The oscillatory motion drives the mount 204 to rotationally oscillate in a plane of motion about an axis of rotation.

The blade mount 204 comprises a housing with a base 210 and two side walls 212 protruding perpendicularly from the edges of the base 210. The base 210 has a base face which lies parallel to the plane of motion. A longitudinal axis of the blade mount 204 runs parallel to the plane of motion and aligns with the longitudinal axis of the attachment 200 when the blade mount 204 is in a neutral position, that is, when the blade mount 204 has not been rotated. The blade mount 204 is symmetrical about a plane of symmetry which is perpendicular to the plane of motion and which lies along the longitudinal axis of the blade mount 204. With the blade mount 204 in neutral position, the side walls 212 run parallel to the longitudinal axis of the blade mount 204 from the end of the blade mount 204 furthest from the connector 202, the distal end of the blade mount 204, towards the end of the blade mount 204 closest to the connector 202 of the attachment 200, the proximal end of the blade mount 204. A top wall 216 protrudes perpendicularly from each of the side walls 212, towards the opposite side wall 212. Each of the side walls and top walls 216 forms, in conjunction with the base 210, a groove 214 which runs from the distal end of the blade mount 204 towards the proximal end of the blade mount 204. The grooves 214 form openings for receiving a blade 100 at the distal end of the mount 204. In addition, each groove 214 is bounded by an upper face. The upper face is the face of the top wall 216 closest to the base 210. The upper face runs parallel to the base face. The distance that each top wall 216 protrudes from the corresponding side wall 212 is uniform for the majority of the length of the side wall 212; however, the distance increases towards the proximal end of the mount 204. Two stabilising members 220 protrude from the base 210 of the mount 204 at the proximal end of the mount 204. Each stabilising member 220 connects with one of the top walls 216, forming two cavities 218. Each cavity 218 opens on to one of the grooves 214. Each cavity 218 is bounded on the outer face by the inward facing face of the side wall 212 and on the inner face by a securing face 222 of the stabilising member 220. Each securing face 222 is angled relative to the longitudinal axis of the blade mount 204 such that the cavities 218 narrow towards the proximal end of the mount 204.

A locking member 230 protrudes perpendicularly from the base 210 of the mount 204. The locking member 230 has a top face running parallel to the base face, two side faces running parallel to the side walls 212, a first inclined face 232 sloping away from the proximal end of the mount 204 where the securing faces 222 are located, and an opposing second inclined face 234 sloping away from the distal end of the mount 204 where the grooves 214 form openings for receiving a blade 100. The first inclined face 232 is a biasing face for urging a blade 100 into the blade mount 204, against the securing faces 222. The second inclined face 234 allows a blade 100, upon insertion into the blade mount 204, to urge the locking member 230 into the base 210 of the blade mount 204 to allow the blade 100 to pass. The locking member 230 may be retracted into the base 210 of the mount 204. One or more springs urge the locking member 230 out of the base 210 and into its protruding position.

A pair of pressure plates 236 protrudes from the base 210, running along each of the side walls of the locking member 230. The pressure plates 236 have top faces that run parallel to the base face of the mount 204. The pressure plates 236 are connected to each other below the locking member 230 such that when the locking member 230 retracts, the pressure plates 236 retract. However, once the locking member 230 is in its protruding position, the pair of pressure plates 236 becomes independently movable and is urged upwards, out of the base, by one or more springs.

The release knob 206 is located on the opposite side of the attachment 200 to the mount 204, in the direction perpendicular to the base face of the mount 204. When the release knob 206 is rotated, the locking member 230 and pressure plates 236 are retracted into the base 210 of the mount 204, releasing any blade 100 previously secured within the mount 204. The release knob 206 is configured such that it is not driven by the rotational motion provided to the mount 204. This reduces the strain on the motor of the hand-piece 20 along with the amount of noise and vibration produced when the saw is in operation.

Figure 4:
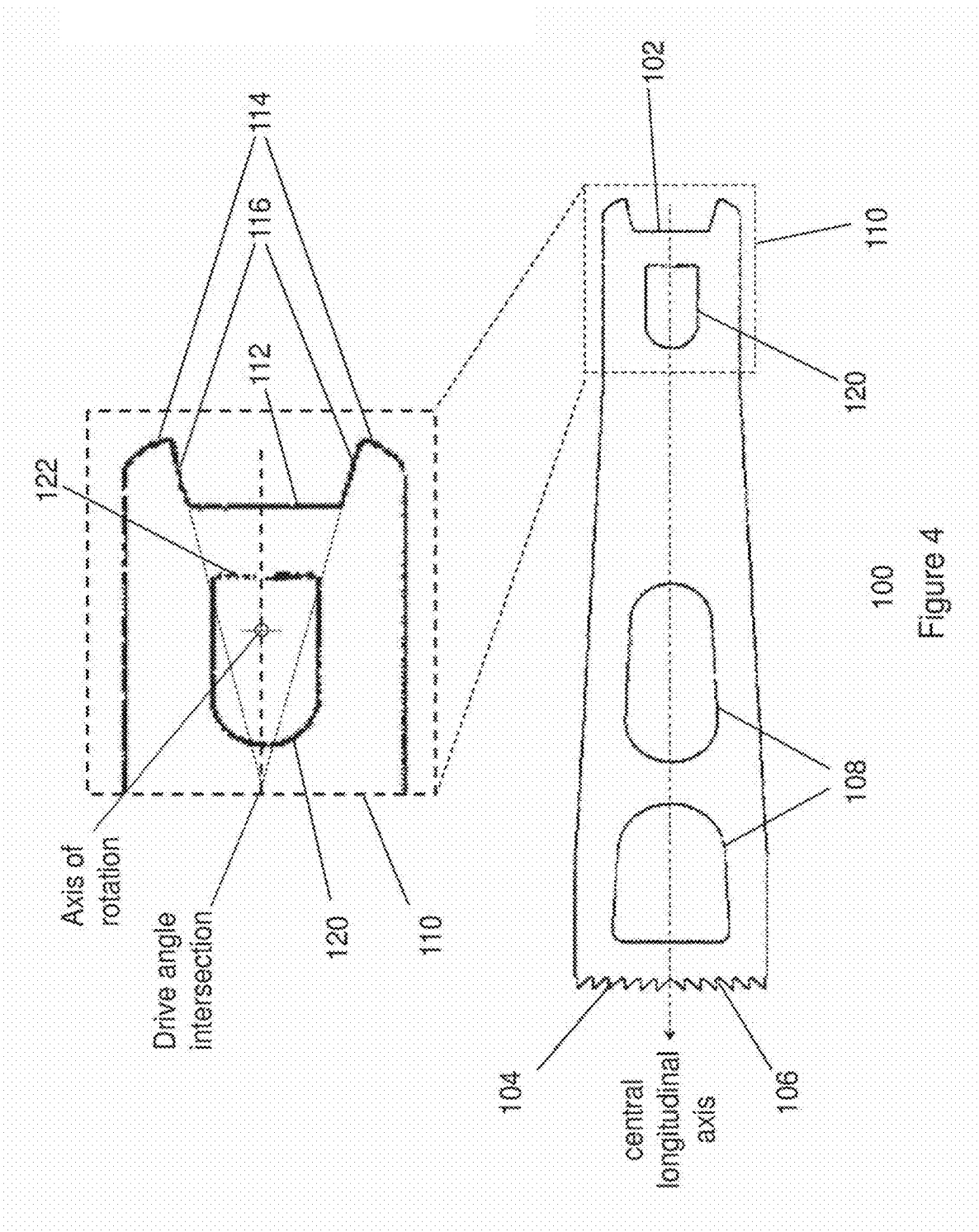
FIG. 4 shows a surgical saw blade 100 in accordance with an embodiment of the invention.

FIG. 4 shows a surgical saw blade 100 in accordance with an embodiment of the invention. The body of the blade is substantially planar defining a plane of the blade. The body of the blade comprises a proximal end 102 and a distal end 104 located on opposites ends of the blade to each other. A central longitudinal axis runs between the proximal end and the distal end bisecting the blade across the plane of the blade. The distal end 104 has a cutting edge 106. The cutting edge 106 is serrated and comprises a set of triangular teeth which protrude from the distal end 104 in a plane parallel to the plane of the blade. Holes 108 may be cut in the main body of the blade 100. These holes 108 reduce the weight of the blade 100 therefore reducing the force required to drive the blade 100. The distribution of the holes 108 may be symmetrical about the central longitudinal axis. The blade 100 shape is usually symmetrical about the central longitudinal axis.

The proximal end 102 forms part of a coupling portion 110 of the blade 100 for removably coupling the blade 100 to an oscillatory tool, such as that shown in FIG. 1. The coupling portion 110 is an attachment hub which may be secured within a blade mount such as that shown in FIG. 3. The coupling portion 110 includes an aperture edge 120 which defines an aperture extending through the body of the blade 100. The aperture forms openings on both of the faces of the blade 100 which run parallel to the plane of the blade 100. The aperture extends through the body of the blade 100 along an axis perpendicular to the plane of the blade 100. The aperture edge 120 defines a lock face 122. The lock face 122 is defined by one axis running perpendicular to the plane of the blade 100 and a second axis running perpendicular to the central longitudinal axis of the blade 100, parallel to the plane of the blade 100. The opposite face to the lock face 122 is curved in the plane of the blade 100. The aperture formed by the aperture edge 120 is symmetrical about the central longitudinal axis allowing the blade 100 to be inserted into a blade mount either way up.

A central proximal edge 112 is located at the centre of the proximal end 102 of the blade 100. The central proximal edge 112 is symmetrical about the central longitudinal axis of the blade. Furthermore, the central proximal edge 112 is slightly longer than, and runs parallel to, the lock face 122. On either side of the central proximal edge 112, two prongs 114 protrude from the proximal end 102 of the blade 100. The prongs 114 protrude in a plane parallel to the plane of the blade 100. The outer edges of the prongs 114 do not extend beyond the width of the main body of coupling portion 110. Furthermore, the pair of prongs 114 is symmetrical about the central longitudinal axis of the blade. Each prong has an inner face 116, the face of the prong closest to the central proximal edge 112. Each inner face 116 is perpendicular to the plane of the blade 100 and is angled relative to the central longitudinal axis. The inner faces 116 slope away from each other at equal and opposite angles relative to the longitudinal axis of the blade 100 such that the transverse distance between the inner faces 116 of the two prongs 114 is greater at the tip of the prongs 114 than at their base. The angle between the two inner faces 116 is 30°. The angle between the longitudinal axis of the blade 100 and each of the inner faces 116 is 15°. Whilst specific angles have been disclosed, it will be understood that a range of angles would achieve the desired results, as detailed by the geometry described below.

The blade 100 is configured to be driven to rotationally oscillate about an axis of rotation by forces exerted at the inner faces 116 of the prongs 114. The blade 100 is configured to rotate in a plane of motion is parallel to the plane of the blade 100. The axis of rotation is perpendicular to the plane of the blade 100 and passes through the aperture defined by the aperture edge 120. The axis of rotation passes through the central longitudinal axis of the blade 100. The inner faces 116 of the blade 100 are positioned and angled such that the projections of the inner faces 116 intersect with each other and with the plane of the blade 100 at a drive angle intersection. The drive angle intersection lies on the central longitudinal axis of the blade 100. The inner faces 116 are angled such that the drive angle intersection is located between the axis of rotation and the distal end 106 of the blade 100. That is, the distance between the drive angle intersection and the proximal end 102 is greater than the distance between the axis of rotation and the proximal end 102. As shall be described later, this geometry means that driving forces applied at the inner faces 116 urge the blade 100 further into a blade mount 204, resulting in a more secure mounting configuration.

The combination of the lock face 122 and the angled inner faces 116 of the prongs 114 allows the blade 100 to be secured and driven by forces exerted in the plane of the blade 100. As the blade 100 is driven to rotationally oscillate in the plane of motion parallel to the plane of the blade 100 it will experience the greatest forces due to motion in the plane of the blade 100. By securing the blade 100 via forces exerted in the plane of the blade 100, mechanical play during motion and wear on the contact faces is reduced and accounted for. Furthermore, the angled inner faces 116 help to positively locate the blade 100 in the correct position when inserted into a blade mount 204.

Figure 5:
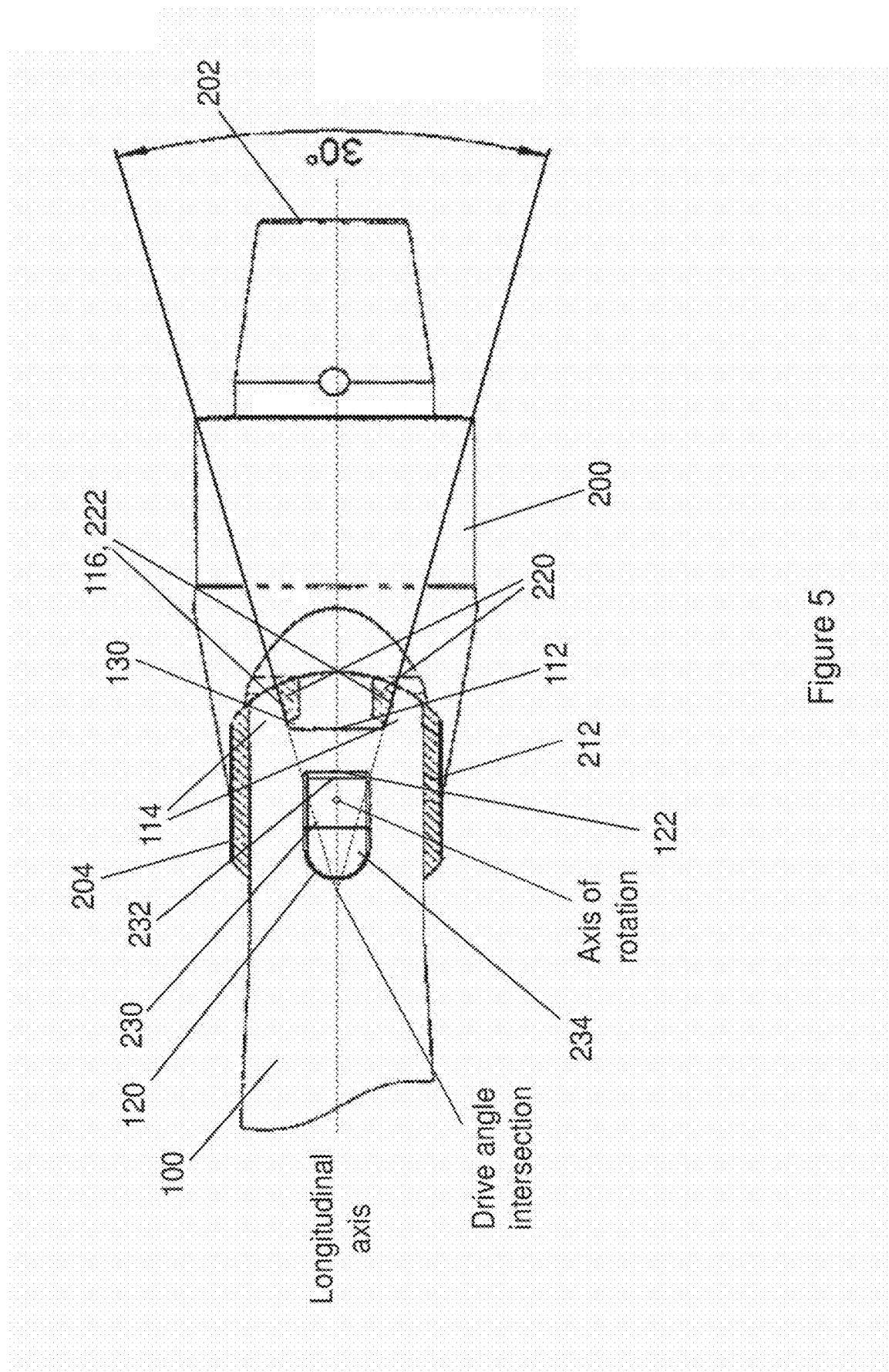
FIG. 5 shows a blade 100 and attachment 200 in accordance with an embodiment of the invention.

FIG. 5 shows a blade 100 and attachment 200 in accordance with an embodiment of the invention. The blade 100 is secured within a blade mount 204. The blade 100 is positioned inside the grooves 214 defined by top walls 216, side walls 212 and base 210 of the blade mount 204. The prongs 114 of the blade 100 fit within the cavities 218 defined by the side walls 212, top walls 216, base 210 and stabilising members 220 of the mount 204. The inner faces 116 of the prongs 114 lie along the securing faces 222 of the stabilising members 220 of the blade mount 204. The locking member 230 is received into the aperture 120 in the blade 100.

Upon full insertion of the blade 100, a gap is left between the central proximal edge 112 of the blade 100 and stabilising members 220. This gap allows the blade 100 and blade mount 204 system to accommodate for wear and manufacturing tolerances. As the faces of the blade 100 and/or blade mount 204 wear down, the gap allows the blade 100 to be urged further into the blade mount 204 by the locking member 230, with each securing face 222 making contact with the inner face 116 of the corresponding prong 114 at a point closer to the base of the prong 114.

The blade mount 204 is configured to rotate about an axis of rotation. The axis of rotation is perpendicular to the base 210 of the blade mount 204 and passes through the locking member 230. The securing faces 222 of the blade mount 204 are angled so that the projections of the two securing faces 222 intersect with each other and with the plane of motion at a drive angle intersection. The distance between the axis of rotation and the proximal end of the blade mount 204 is shorter than the distance between the drive angle intersection and the proximal end of the blade mount 204. Advantageously, the angle between the two projections of the inner faces is 30°; however, it will be recognised that a range of different angles may be employed in accordance with embodiments of the invention.

Figures 6A, 6B:
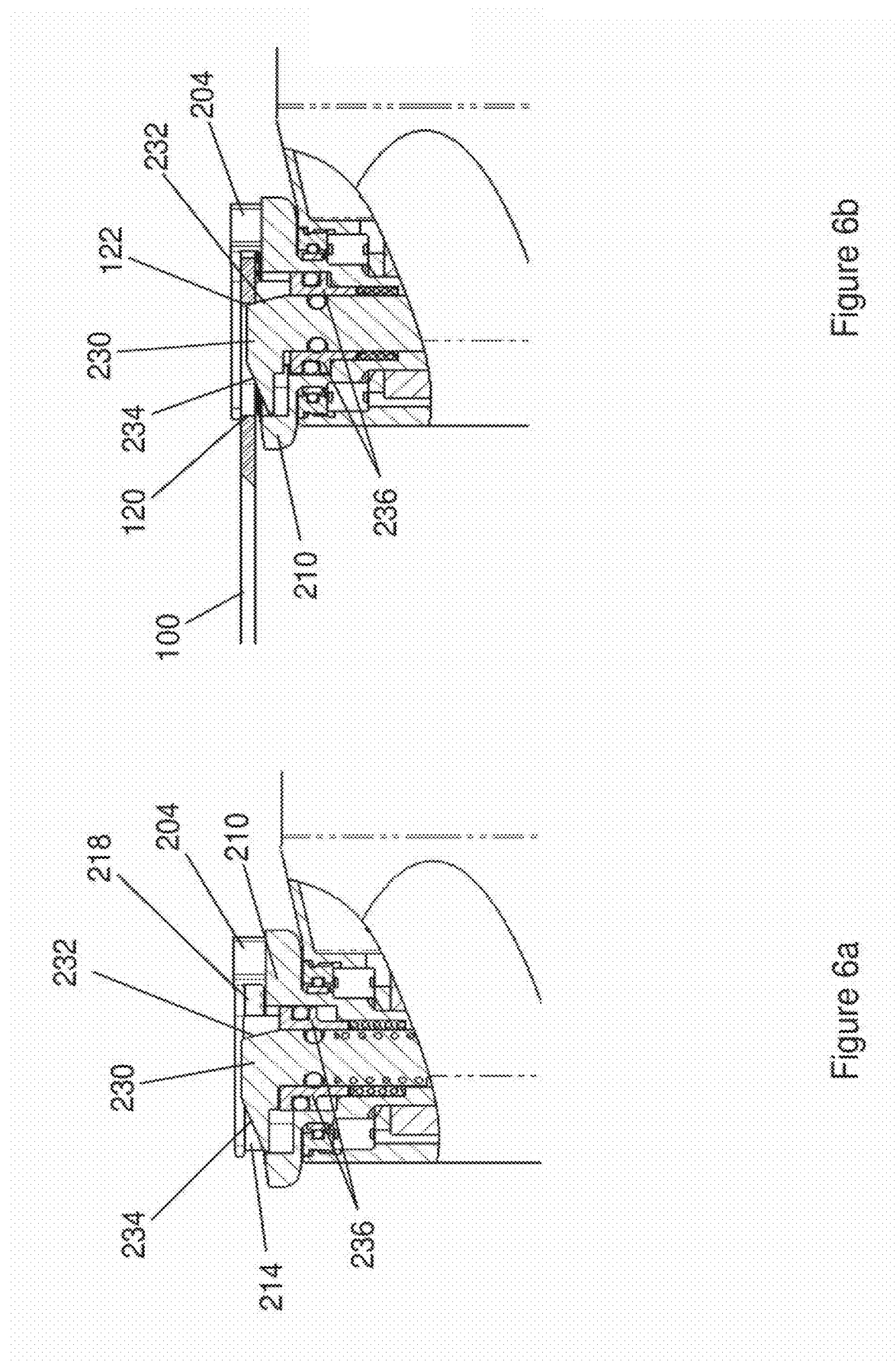
FIG. 6a shows a cross-sectional side view of a blade mount 204 in accordance with an embodiment of the invention.
FIG. 6b shows a cross-sectional side view of a blade mount 204 securing a blade 100 in accordance with an embodiment of the invention.

FIG. 6a shows a cross-sectional side view of a blade mount 204 in accordance with an embodiment of the invention. The locking member 230 is urged out of the base 210 of the blade mount 204 by springs. The locking member 230 is urged in a direction perpendicular to the base face of the blade mount 204. The locking member 230 has a first inclined face 232 which slopes away from the proximal end of the blade mount 204 where the securing faces 222 are located. The longitudinal distance from the first inclined face 232 to the proximal end of the blade mount 204 increases as the perpendicular distance from the base 210 of the blade mount 204 increases. On the opposite side of the locking member 230 to the first inclined face 232 is a second inclined face 234 which slopes away from the distal end of the blade mount 204 where the grooves 214 form openings to allow the blade to be inserted into the blade mount 204. The longitudinal distance from the first inclined face 232 to the distal end of the blade mount 204 increases as the perpendicular distance from the base 210 of the blade mount 204 increases. The pressure plates 236 include portions which extend underneath part of the locking member 230. The pressure plates 236 are urged out of the base 210 of the blade mount 204, in a direction perpendicular to the base face. When the blade mount 204 is empty, the pressure plates 236 are urged against the underside of the locking member 230.

FIG. 6b shows a cross-sectional side view of a blade mount 204 securing a blade 100 in accordance with an embodiment of the invention. As a blade 100 is inserted into the blade mount 204, along the grooves 214, the central proximal edge 112 of the blade 100 makes contact with the second inclined face 234 of the locking member 230. As the blade 100 moves into the blade mount 204 the central proximal edge 112 slides along the second inclined face 234 and urges the locking member 230 into the base 210 of the blade mount 204, thereby moving the locking member 230 out of the path of the blade 100. As the locking member 230 is depressed, the underside of the locking member 230 urges the pressure plates 236 into the base 210 of the blade mount 204. This mechanism allows the blade 100 to be inserted past the locking member 230 and pressure plates 236.

As the blade 100 is inserted towards its final secured position, the aperture 120 of the blade aligns with the locking member 230. Once aligned, the locking member 230 is urged into the aperture 120 of the blade 100. As the locking member 230 is urged into the aperture 120, the first inclined face 232 of the locking member 230 applies pressure to the lock face 122 of the blade 100. The first inclined face 232 urges the blade 100 further into the blade mount 204, against the securing faces 222. This action secures the blade 100 in place and biases the blade 100 against the securing faces 222. The first inclined face 232 also urges the blade 100 against the top walls 216 of the blade mount 204. This action helps to clamp the blade 100 in place.

As the locking member 230 moves out of the base 210 and into the aperture 120, the pressure plates 236 are also urged upwards. As the locking member 230 may move into the aperture 120, but the pressure plates 236 may not, the pressure plates 236 do not extend as far as the locking member 230. There is therefore a gap between the underside of the locking member 230 and the pressure plates 236 which allows the pressure plates 236 to apply additional forces which bias the blade 100 against the upper faces of the grooves 214, helping the locking member 230 to clamp the blade 100 in position. Whilst a pair of pressure plates is described, it should be noted that a single pressure plate may achieve the same purpose.

The correct insertion of the blade 100 is aided by the locking member 230 urging the blade 100 into position, as well as the angled securing faces 222 of the stabilising members 220 helping the blade 100 to slide into the correct alignment. The correct insertion of the blade is further supported by the lock face 122 of the aperture edge 120 receiving the biasing force and the angled inner faces 116 of the prongs 114 of the blade 100 allowing the blade 100 to slide into the cavities 218 in the side walls 212 of the mount 204.

Figure 7:
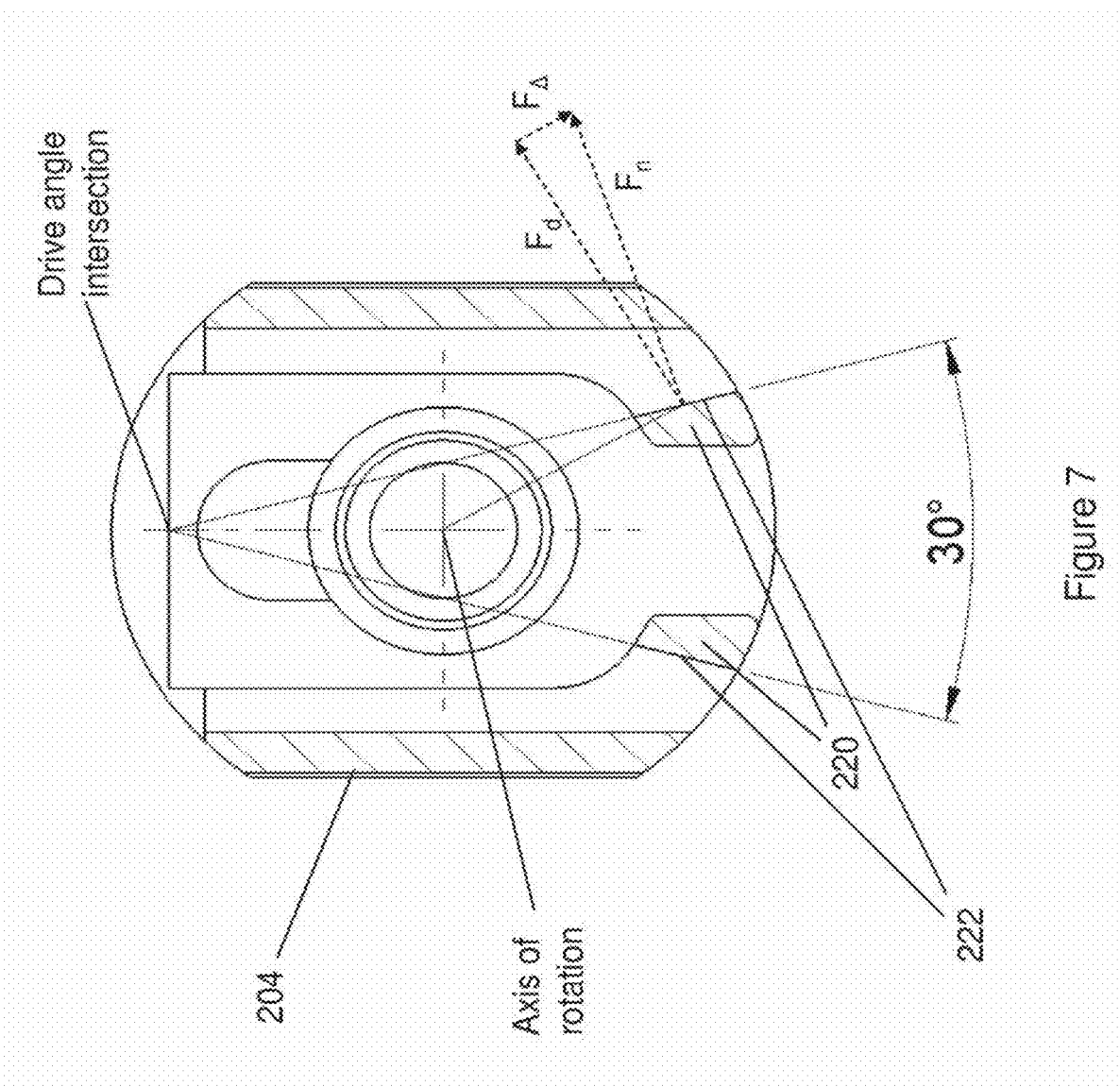
FIG. 7 shows a coupling portion 110 of a blade 100 mounted within a blade mount 204 in accordance with an embodiment of the invention.

FIG. 7 shows a blade mount 204 in accordance with an embodiment of the invention. The blade mount 204 is driven to rotate about an axis of rotation which is perpendicular to the base face of the blade mount 204. The axis of rotation passes through the locking member 230 of the blade mount 204. The securing faces 222 are configured to drive a blade 100 (as shown in FIG. 4), urging the blade at the inner faces 116 of the prongs 114 of the blade 100. The blade 100 is configured to rotate about an axis of rotation which is perpendicular to the plane of the blade. In addition, the axis of rotation passes through the aperture defined by the aperture edge 120 of the blade 100. The securing faces 222, and correspondingly, the inner faces 116 of the blade 100, are angled 15° from the longitudinal axis of the blade mount 204 such that the projections of the securing faces 222 and the projections of the inner faces 116 meet at a drive angle intersection which is located distally to the axis of rotation. It will be understood that, where the axis of rotation is located further from the securing faces 222, or the inner faces 116 of the blade 100, the drive angle intersection may need to be located further from the securing faces 222 or inner faces 116 and therefore, the angle between said faces and the longitudinal axis would be more acute.

By driving at an angle such that the drive angle intersection is located on the far side of the axis of rotation from the securing faces 222 and the inner faces 116, the blade 100 is forced further into the blade mount 204, providing a more stable drive. As each of the securing faces 222 is driving, each securing face 222 exerts a force, $F_n$, parallel to the normals of the securing face 222 and the inner face 116. As the system is urged about the axis of rotation, each point along the inner face 116 experiences a driving force, $F_d$, directed along the direction of rotation. The driving force, $F_d$, is the projection of the total force, $F_n$, along the direction of rotation at that specific point. The direction of rotation is perpendicular to the radius linking the axis of rotation to the point that the driving force, $F_d$, is being exerted. The driving forces, $F_d$, result in the blade 100 being driven to rotate about the axis of rotation. As the securing faces 222 and the inner faces 116 do not lie along the radius of rotation, the total force, $F_n$, exerted by the securing faces 222 is not directed along the direction of rotation. The difference between the total force, $F_n$, exerted by the securing face 222 on the inner face 116 and the driving force, $F_d$, which results in the blade 100 being rotated, is accounted for by a third force, $F_\Delta$:

$$F_n = F_d + F_\Delta$$

The third force, $F_\Delta$, may be countered by friction between the blade 100 and the blade mount 204. As the inner faces 116/securing faces 222 are angled such that the axis of rotation is positioned between the drive angle intersection and the proximal end of the blade 100/blade mount 204, the third force, $F_\Delta$, is directed such that it urges the blade further into the blade mount 204. This biases the blade 100 against the blade mount 204 providing a more secure drive. If the drive angle intersection was located between the axis of rotation and the proximal end of the blade 100/blade mount 204, the third force, $F_\Delta$, would be directed out of the blade mount 204 and would therefore urge the blade 100 out of the blade mount 204 and away from the securing faces 222.

Each blade 100 is designed to have an axis of rotation which passes through the aperture of the blade 100. By angling the inner faces 116 of the prongs 114 of the blade 100 such that the projections of the inner faces 116 meet at a point which is located between the distal end 104 of the blade 100 and the axis of rotation, the blade 100 may be driven by a system such as that described above. Such a blade 100 may therefore benefit from a more secure mounting system with reduced play as it is driven. In this arrangement, the distance between the proximal end 102 of the blade 100 and the drive angle intersection is greater than the distance between the proximal end 102 of the blade 100 and the axis of rotation.

The combination of the locking member 230 and the securing faces 222 provides a strong support for the blade 100, reducing play as the blade 100 is driven. The locking member 230 provides a securing force which urges the blade 100 along the longitudinal axis of the blade mount 204 towards the securing faces 222. The securing force presses the inner faces 116 of the prongs 114 of the blade 100 against the securing faces 222 of the blade mount 204. The securing faces 222 convert this longitudinal force into a transverse force, providing additional stability in the plane in which the blade 100 is driven. This is particularly important as the greatest forces which the blade 100 experiences whilst being driven will be in the plane of the blade 100.

An additional advantage of above arrangement is that it accounts for manufacturing tolerances as well as wear through repeated use. The biasing face 232 and the securing faces 222 of the blade mount 204 and the inner faces 116 and lock face 122 of the blade 100 are likely to experience a large amount of stress during use and may rub against each other. There is therefore a risk that these faces will wear down through repeated use. This wear is accommodated for by the biasing from the locking member 230. As the biasing face 232 of the blade mount 204 and/or the lock face 122 of the blade 100 wear down, the locking member 230 can be urged further out of the base 210 of the blade mount 204 in order to accommodate. Furthermore, as the stabilising faces 222 of the blade mount 204 and/or the inner faces 116 of the blade 100 wear down, the blade 100 can be urged further into the holder by the locking member 230. The stabilising faces 222 would therefore sit further down the inner faces 116 of the prongs 114 of the blade 100. The longitudinal force in the plane of the blade provided by the locking member 230 therefore accounts for wear between the faces of the blade 100 and the blade mount 204. The lock face 122 allows a longitudinal force to be applied to the blade 100 as it runs perpendicular to the longitudinal axis of the blade 100. This arrangement provides a more secure fit, reducing play in the blade 100 during motion and increasing cutting efficiency whilst also reducing wear.

Figure 8:
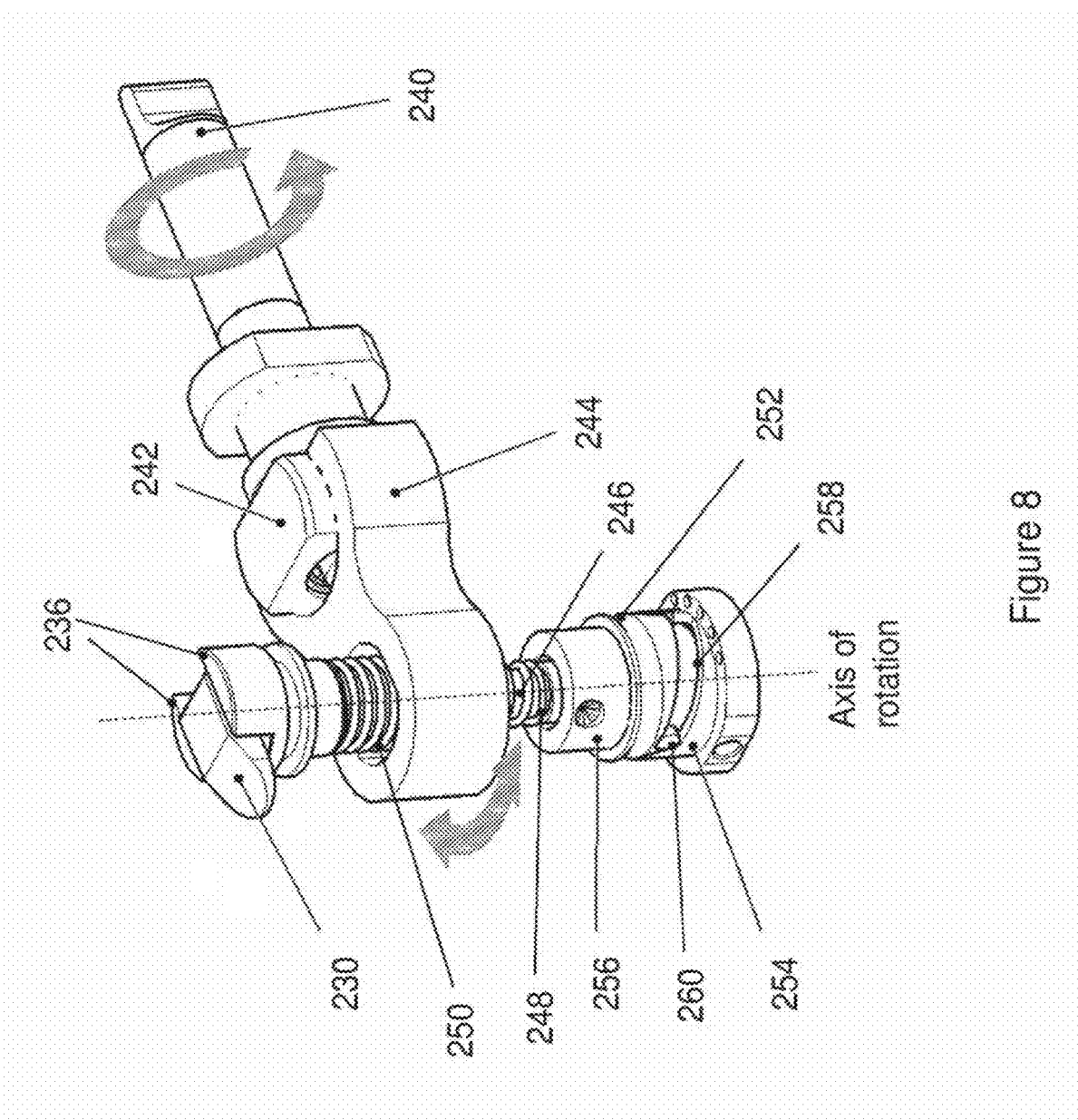
FIG. 8 shows an internal drive and release mechanism for an attachment 200 in accordance with an embodiment of the invention; and, FIG. 9 shows a cross-sectional view of an attachment 200 in accordance with an embodiment of the invention.

FIG. 8 shows an internal drive and release mechanism for an attachment 200 in accordance with an embodiment of the invention. The mechanism is suitable for converting a rotary drive into a rotational oscillation. In addition, the mechanism allows the blade mount 204 to be isolated from the release mechanism 252, reducing the mass which needs to be driven.

The mechanism converts a rotary motion, which may be provided by a handpiece 20, into a rotational oscillation. A rotary drive is provided to an eccentric spindle 240. As the eccentric spindle 240 rotates, it drives a drive bush 242 which runs in a fork 244. With each rotation of the eccentric spindle 240 the fork 244 oscillates from side to side about an axis of rotation centred on a locking shaft 246. The longitudinal axis of the locking shaft 246 is parallel to, and lies along, the axis of rotation. The locking shaft 246 is driven to rotate by the fork 244.

The locking shaft 246 runs from the locking member 230 towards a release mechanism 252. The locking shaft 246 and locking member 230 are urged out of the base 210 of the blade mount 204 by a first spring 248 which encircles a portion of the locking shaft 246. Two pressure plates 236 are positioned either side of the locking shaft 246. The pressure plates 236 are connected beneath the locking member 230. The pressure plates 236 comprise a portion which extends underneath the locking member 230, on the side of the locking member 230 which connects to the locking shaft 246. This portion of the pressure plates 236 means that the pressure plates 236 may be depressed by the locking member 230 when the locking member 230 is depressed. The pressure plates 236 are urged out of the base 210 of the blade mount 204 by a second spring 250 which encircles a portion of the locking shaft 246.

The fork 244 drives the locking shaft 246, the locking member 230, the pressure plates 236, the two springs 248, 250 and the blade mount 204 to oscillate about the axis of rotation which is centred on the locking shaft 246. The axis of rotation lies along a plane perpendicular to the base face of the blade mount 204.

The locking shaft 246 and locking member 230 may be retracted into the base 210 of the blade mount 204 by the release mechanism 252. The release mechanism 252 is separated from the locking shaft 246 such that it isn't driven by the fork 244. This reduces the mass which must be driven and decreases the number of moving parts which results in a system which is more efficient and which causes less vibration and noise during use. The release knob 206 is connected to a cam guide 254. The cam guide 254 is toroidal and encircles an outer release ring 256. The outer release ring 256 is toroidal and encircles the lock shaft 246. The cam guide 254 and outer release ring 256 are located at the opposite end of the lock shaft 246 to the locking member 230. The cam guide 254 and outer release ring 256 are concentric with each other and with the longitudinal axis of the cylindrical locking shaft 230.

The cam guide 254 has a helical channel 258 in which a pin 260 sits. The pin 252 is a member which protrudes radially outwards from the outer face of the outer release ring 256. As the release knob 206 is rotated the cam is urged away from the blade mount 204, along the longitudinal axis of the helical channel 258, moving the outer release ring 256 away from the blade mount 204 in a direction parallel to the longitudinal axis of the locking shaft 246. The outer release ring 256 urges the locking shaft 246 away from the blade mount 204, thereby retracting the locking member 230 into the base 210 of the blade mount 204.

FIG. 9 shows a cross-sectional view of an attachment 200 in accordance with an embodiment of the invention. The eccentric spindle 240 passes through the centre of the attachment 200, parallel to the longitudinal axis of the attachment 200. The locking shaft 246 runs perpendicular to the base 210 of the blade mount 204, between the blade mount 204 and the release knob 206.

An inner release ring 262 is connected to the locking shaft 246 at the opposite end of the shaft to the locking member 230. The inner release ring 262 is toroidal and is positioned within the outer release ring 256. When the release mechanism 252 is in a locked position the outer release ring 256 is isolated from the inner release ring 262 such that the two components do not touch. The inner release ring 262 comprises an inner release member 264 which protrudes towards the outer release ring 256. The inner release member 264 protrudes radially from the inner release ring 262, away from the axis of rotation and the longitudinal axis of the locking shaft 246. The outer release ring 256 has an outer release member 266 which protrudes towards the inner release ring 262. The outer release member 266 protrudes radially from the outer release ring 262, towards the axis of rotation and the longitudinal axis of the locking shaft 246. The locking member 230 is closer to the outer release member 266 than the inner release member 244. This means that when the outer release ring 262 is moved away from the locking member 230, the outer release member 266 makes contact with the inner release member 264 and urges the inner release ring 262 and locking shaft 246 away from the blade mount 204. This moves the locking member 230 into the base 210 of the blade mount 204. When a blade 100 is secured within the blade mount 204 this action therefore releases the blade 100 allowing the blade 100 to be removed.

Whilst certain embodiments have been described above, the embodiments have been presented by way of example only and are not intended to limit the scope of protection. It should be understood that the invention is not limited to the specific aspects and embodiments described above and that a variety of modifications, additions and deletions are within the scope of the invention as defined by the following claims.

The invention claimed is:

1. A surgical saw blade comprising:
a substantially planar body comprising a distal and a proximal end defining a longitudinal axis lying in the plane of the blade;
the distal end having a cutting edge;
the proximal end forming part of a coupling portion for removably coupling the blade to an oscillatory power tool, the coupling portion being configured to be driven such that the blade rotationally oscillates about an axis of rotation running perpendicular to the plane of the blade and crossing the plane of the blade at a point of rotation;
the coupling portion comprising:
a lock face perpendicular to the longitudinal axis of the blade and passing through the plane of the blade, the lock face forming part of a boundary of an aperture, the aperture extending through the plane of the blade and wherein the lock face is configured to receive a securing force directed parallel to the longitudinal axis, towards the proximal end of the blade; and
two prongs protruding from the proximal end of the blade, each prong comprising an inner face, the inner faces being angled relative to the longitudinal axis of the blade such that the planes of the inner faces intersect with each other and with the plane of blade at a point of intersection located between the axis of rotation and the distal end of the blade, wherein the angle in the plane of the blade between the two planes of the inner faces at the point of intersection is less than 40°.

2. The blade of claim 1, wherein the angle in the plane of the blade between the two planes of the inner faces at the point of intersection is greater than 20°.

3. The blade of claim 1, wherein the angle in the plane of the blade between the two planes of the inner faces at the point of intersection is greater than 25° and/or less than 35°.

4. The blade of claim 1, wherein the angle in the plane of the blade between the two planes of the inner faces at the point of intersection is greater than 28° and/or less than 32°.

5. The blade of claim 1, wherein the lock face is configured to receive a securing force directed parallel to the longitudinal axis, towards the proximal end of the blade.

6. The blade of claim 5, wherein the inner faces of the blade are configured to be biased against one or more securing faces of a blade mount by the securing force such that a portion of the securing force is converted into two opposite transverse forces directed away from each other, parallel to the plane of the blade and perpendicular to the longitudinal axis of the blade.

* * * * *